United States Patent [19]

Clark, III

[11] 4,030,503
[45] June 21, 1977

[54] EMBOLECTOMY CATHETER

[76] Inventor: William T. Clark, III, 6 Davis Blvd., New Orleans, La. 70121

[22] Filed: Nov. 5, 1975

[21] Appl. No.: 628,982

[52] U.S. Cl. .............................. 128/304; 128/356
[51] Int. Cl.² .................................... A61B 17/22
[58] Field of Search ........... 128/303 R, 304, 305 R, 128/311, 328, 341, 348–351, 356, 2 B; 15/104.16

[56] References Cited

UNITED STATES PATENTS

| 584,407 | 6/1897 | Saint Cyr | 128/304 |
| 707,031 | 8/1902 | Spaulding | 128/304 |
| 812,020 | 2/1906 | Crippen | 27/24 A |
| 843,951 | 2/1907 | Klock | 128/356 |
| 1,888,349 | 11/1932 | Jacoby | 128/349 R |
| 2,756,752 | 7/1956 | Scherlis | 128/303 R |
| 3,613,664 | 10/1971 | Willson et al. | 128/2 B |
| 3,749,085 | 7/1973 | Willson et al. | 128/2 B |

OTHER PUBLICATIONS

Shaw – Jour. Bone & Joint Surg., vol. 41–A, No. 4, June 1959, pp. 666–667.

Primary Examiner—Dalton L. Truluck

[57] ABSTRACT

A spiral helix is affixed on the distal end of a flexible catheter.

8 Claims, 8 Drawing Figures

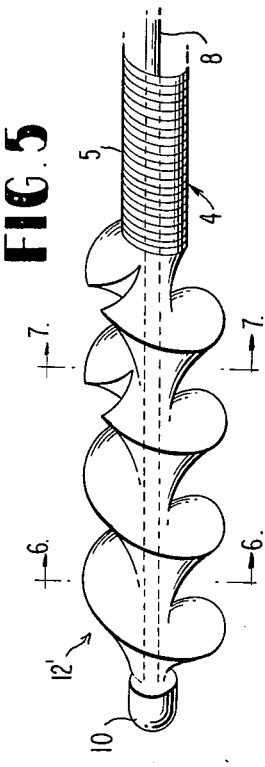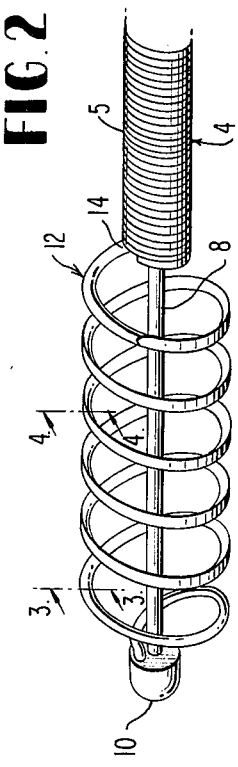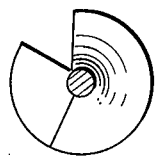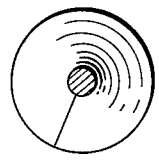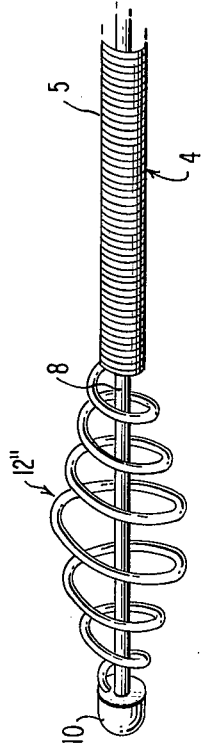

EMBOLECTOMY CATHETER

FIELD OF SEARCH

Surgery, Cannula, Catheter.

OBJECTS

The object of this invention is to provide a means of safely opening and enlarging the lumen of throbbosed blood vessels in the human vascular system. The instrument may be used to open a totally-occluded vessel, or it may be used to enlarge the blood passageway of a very constricted vessel. The instrument is particularly useful for opening arterio-venous shunt vessels narrowed as a result of long-term chronic hemodialysis.

More specifically, it is intended now to provide a flexible catheter having on the distal end thereof a helix or a spiral helix, which is introduced into the blood vessel at a point below the obstruction—a narrowing or clot (thrombus). The catheter is rotated and pushed forward into the clot. The helix screws into the clot, and when it is firmly embedded or has passed the clot, the catheter is pulled out of the vessel without rotation. The clot is thereby dislodged and comes out with the catheter. In general, the catheter operates like a corkscrew.

These and other objects will be apparent from the following specification and drawing, in which:

FIG. 1 is a side elevation of the catheter;
FIG. 2 is an enlarged view of the distal end of the catheter;
FIGS. 3 and 4 are cross-sections along the lines 3—3 and 4—4 of FIG. 2, respectively;
FIG. 5 is a view similar to FIG. 2, but showing the distal end of a modified form of the catheter;
FIGS. 6 and 7 are cross-sections long the lines 6—6 and 7—7, respectively, of FIG. 5; and,
FIG. 8 is an enlarged view of the distal end of a second modified form of the catheter.

Referring first to FIGS. 1-4 of the drawing, the catheter 2 consists of a flexible shaft 4 consisting of a sleeve 5 which may be formed of spirally wound stainless steel springy wire, having a handle 6 secured to its rear end. Included as part of the flexible shaft is flexible spring wire 8 which extends from the handle through and beyond the forward end of the flexible shaft, and a rounded knob 10 is secured on the forward end of the wire.

Connected to wire 8 and extending rearwardly from knob 10 is a helix 12 whose rear end 14 is attached to wire 8. While the helix may be formed of either round wire or wire with a flat outer side, a preferred form incorporates a wire that is round (FIG. 3) at the forward portion of the helix to prevent unintentional forward cutting, and whose outer side is flat (FIG. 4) at the rear portion of the helix. The flatted portion of the wire provides a cutting action when the catheter is withdrawn.

FIGS. 5-7 illustrate a modified form of the helix. Helix 12' is machined to rigid screw form, the screw root being attached to wire 8. The turns of the screw may be solid (FIG. 6) or they may be slotted (FIG. 7) to enhance their cutting action. Where the turns are both plain and slotted, it is preferred that the forward ones be plain so as to inhibit unintentional forward cutting, and that the rear turns be slotted so as to enhance cutting action when the catheter is withdrawn.

The spiral helix incorporated in the FIG. 8 embodiment is generaly like the helix 12 shown in FIGS. 1-4, except in that it is tapered at both ends to facillitate entry and withdrawal.

Various types of helical cutters may be used to advantage with this invention. Those illustrated are examples. The instrument should be constructed of tissue-inert materials which can be sterilized. Silver and stainless steel are well-suited for the helix.

The wire 8 provides control against deformation of the helix and enhances the safety and manipulatability of the device. However, it does increase stiffness and, hence, in a catheter which must negotiate sharp or compound turns, wire 8 would not be incorporated, and the knob 10 would be attached directly onto the end of the helix. The same modification would also be used in a catheter designed for use in very small vessels, for example, when the helix is about .04 inch or smaller in diameter. Alternatively, the wire 8 may be retained in a more flexible catheter by attaching the helix at its forward end to knob 10 and at its rear end to sleeve 5.

I claim:
1. A thrombolectomy catheter comprising
a flexible shaft having forward and rear ends,
a handle on the rear end of the shaft,
a wire having a forward extremity extending beyond the forward end of the flexible shaft,
a rounded blunt member on the forward extremity of the wire, and
a spiral helix surrounding the forwardly-projecting portion of the wire and extending rearwardly from the rounded blunt member the forward portion of said helix having a rounded forwardly-disposed surface, and said helix having a sharp rearwardly-disposed outer edge portion.

2. A thrombolectomy catheter as claimed in claim 1, said spiral helix comprising a wire secured to the rounded blunt member.

3. A thrombolectomy catheter as claimed in claim 2, the wire in at least a portion of the helix which is adjacent the rounded blunt member being of substantially round cross section.

4. A thrombolectomy catheter comprising
a flexible shaft having forward and rear ends,
a handle on the rear end of the shaft,
a rounded blunt member on the forward extremity of the flexible shaft, and
a spiral helix extending rearwardly from the rounded blunt member on the forward end portion of said shaft, said spiral helix comprising a wire, said wire in at least a portion of the helix which is adjacent the rounded blunt member being of substantially round cross section, said wire in at least a portion of said helix which is adjacent the end thereof which is remote from the rounded blunt member having a flat outer side.

5. A thrombolectomy catheter as claimed in claim 2, said helix having inwardly tapered opposite ends.

6. A thrombolectomy catheter as claimed in claim 1, said helix being a rigid screw.

7. A thrombolectomy catheter as claimed in claim 6, wherein at least some of the turns are slotted.

8. A thrombolectomy catheter comprising
a flexible shaft having forward and rear ends,
a handle on the rear end of the shaft,
a rounded blunt member on the forward extremity of the flexible shaft, and
a spiral helix extending rearwardly from the rounded blunt member on the forward end portion of said shaft, said helix being a rigid screw, wherein the turns of the screw which are adjacent the rounded blunt members are continuous and at least some of the turns which are remote from the solid blunt member are slotted.

* * * * *

UNITED STATES PATENT AND TRADEMARK OFFICE
CERTIFICATE OF CORRECTION

PATENT NO. : 4,030,503
DATED : June 21, 1977
INVENTOR(S) : William T. Clark, III It is certified that error appears in the above-identified patent and that said Letters Patent are hereby corrected as shown below:

```
Change the title to:  --THROMBECTOMY CATHETER--.
Line 9, column 1, change "throbbossed" to --thrombosed--.
line 67, column 1, change "facillitate" to --facilitate--.
Claims 1-7, line 1, change "thrombolectomy" to
        --thrombectomy--.
```

Signed and Sealed this

Fifteenth Day of November 1977

[SEAL]

Attest:

RUTH C. MASON
Attesting Officer

LUTRELLE F. PARKER
Acting Commissioner of Patents and Trademarks